(12) United States Patent
Ogawa et al.

(10) Patent No.: US 11,386,920 B2
(45) Date of Patent: Jul. 12, 2022

(54) INTERACTIVE GROUP SESSION COMPUTING SYSTEMS AND RELATED METHODS

(71) Applicant: FACET LABS, LLC, Los Gatos, CA (US)

(72) Inventors: Stuart Ogawa, Los Gatos, CA (US); Lindsay Sparks, Seattle, WA (US); Koichi Nishimura, San Jose, CA (US); Wilfred P. So, Mississauga (CA); Jane W. Chen, Los Gatos, CA (US)

(73) Assignee: FACET LABS, LLC, Los Gatos, CA (US)

( * ) Notice: Subject to any disclaimer, the term of this patent is extended or adjusted under 35 U.S.C. 154(b) by 0 days.

(21) Appl. No.: 17/294,118

(22) PCT Filed: Nov. 15, 2019

(86) PCT No.: PCT/US2019/061599
§ 371 (c)(1),
(2) Date: May 14, 2021

(87) PCT Pub. No.: WO2020/102620
PCT Pub. Date: May 22, 2020

(65) Prior Publication Data
US 2022/0020390 A1    Jan. 20, 2022

Related U.S. Application Data

(60) Provisional application No. 62/768,183, filed on Nov. 16, 2018.

(51) Int. Cl.
*G10L 25/63* (2013.01)
*G16H 20/70* (2018.01)
*G06V 40/16* (2022.01)
*G06V 40/20* (2022.01)
(Continued)

(52) U.S. Cl.
CPC .......... *G10L 25/63* (2013.01); *G06V 40/174* (2022.01); *G06V 40/20* (2022.01); *G10L 15/083* (2013.01); *G10L 25/78* (2013.01); *G16H 20/70* (2018.01); *G10L 2025/783* (2013.01)

(58) Field of Classification Search
CPC .............................. G10L 25/63; G16H 20/70
See application file for complete search history.

(56) References Cited

U.S. PATENT DOCUMENTS

| 2015/0215350 | A1* | 7/2015 | Slayton | G06F 9/453 |
| | | | | 709/204 |
| 2017/0357901 | A1* | 12/2017 | La Placa | G06Q 40/06 |
| 2018/0052926 | A1* | 2/2018 | Boudville | G06F 16/951 |

(Continued)

*Primary Examiner* — Bryan S Blankenagel

(57) ABSTRACT

Assistive technologies are herein provided to assist leaders in engaging one or more group participants using a combination of private data specific to a participant and public data specific to a participant. The system includes: a group bot that has public group data and private group data, a first bot for a first participant that has private data and public data associated with the first participant, and a leader bot for a leader. The leader bot is data interactive with the group bot and the first bot, and can cause the first bot to appropriately serve private data on a permissioned private device of the first participant and to serve public data on a permissioned group output device.

26 Claims, 11 Drawing Sheets

(51) Int. Cl.
  *G10L 15/08* (2006.01)
  *G10L 25/78* (2013.01)

(56) References Cited

U.S. PATENT DOCUMENTS

2019/0124049 A1* 4/2019 Bradley ................ H04W 76/14
2019/0238354 A1* 8/2019 Wiener ............... H04L 12/1831
2020/0127988 A1* 4/2020 Bradley .................. H04L 63/08

* cited by examiner

INTERACTIVE GROUP SESSION COMPUTING SYSTEMS AND RELATED METHODS

CROSS-REFERENCE TO RELATED APPLICATION

This patent application claims priority to U.S. Provisional Patent Application No. 62/768,183 filed on Nov. 16, 2018 and titled "Interactive Group Session Computing Systems and Methods", the entire contents of which are herein incorporated by reference.

TECHNICAL FIELD

The following generally relates to interactive assistive devices and related computing architectures and methods for processing data and outputting user feedback, such as via audio or visual media, or both, to respond to the emotions and behaviors of people in a group session setting.

DESCRIPTION OF THE RELATED ART

People sometimes experience emotions related to fear, uncertainty, doubt and agitation. These emotions can damage the emotional well-being and the physical well-being of the person and can affect the people that support that person. These negative emotions can be caused by different reasons, including and not limited to dementia, Alzheimer's disease, post-traumatic stress disorder, depression, addiction, cognitive degeneration, brain injury, bipolar disorder, autism, down syndrome, attention deficit hyperactivity disorder, hormonal imbalances, memory loss due to aging, episodic amnesia and situational events.

People participate in group therapy and activities in order to directly or indirectly address, manage, or cope with these emotions, cognitive health and physical health. People also participate in group therapy and activities to learn, to find support from others, and to help people relate to others. In group therapy or activity session, a group leader (e.g. a therapist, a caregiver, an activity coordinator, etc.) leads a discussion or an activity, or both, amongst the group participants. A person may participate in multiple group sessions with one or more group leaders. Sometimes, a series of group sessions is led by different group leaders.

Typically, a group leader prepares for a group session by preparing notes about the activities or discussions, or both. The group leader may also take notes during the discussion and afterwards. Group leaders also try to be effective by understanding the progression of individual participants. Sometimes leading a group is difficult since group participants act out in disruptive ways (e.g. yelling, swearing, physically violent, etc.) or participants are unengaged (e.g. stay quiet, do not participate in the activity, etc.). It can be understood that running a group session, or a series of group sessions, is challenging for the group leader as they try to effectively help the group participants while managing different aspects of the group session.

Currently, most group leaders prefer to use very simple tools, like pen and paper to make notes, since these are very easy to use. Some group leaders may use a laptop to make notes, but this is cumbersome and distracting. Tablet computers with stylus pens or touch screen keyboards are also sometimes used, but still are difficult to use when the group leader is trying to give their full attention to one or more group participants. Using these technologies or tools in a stressful moment, such as during a disruption from a group participant, is impractical.

These above challenges, and other technical challenges, lead to limited adoption of assistive devices during group sessions. These challenges also apply to other types of group sessions and non-limiting examples include a trainer working with a group of trainees, and a teacher that teaches a group of students.

BRIEF DESCRIPTION OF THE DRAWINGS

Embodiments will now be described by way of example only with reference to the appended drawings wherein.

DETAILED DESCRIPTION

Figure 1:
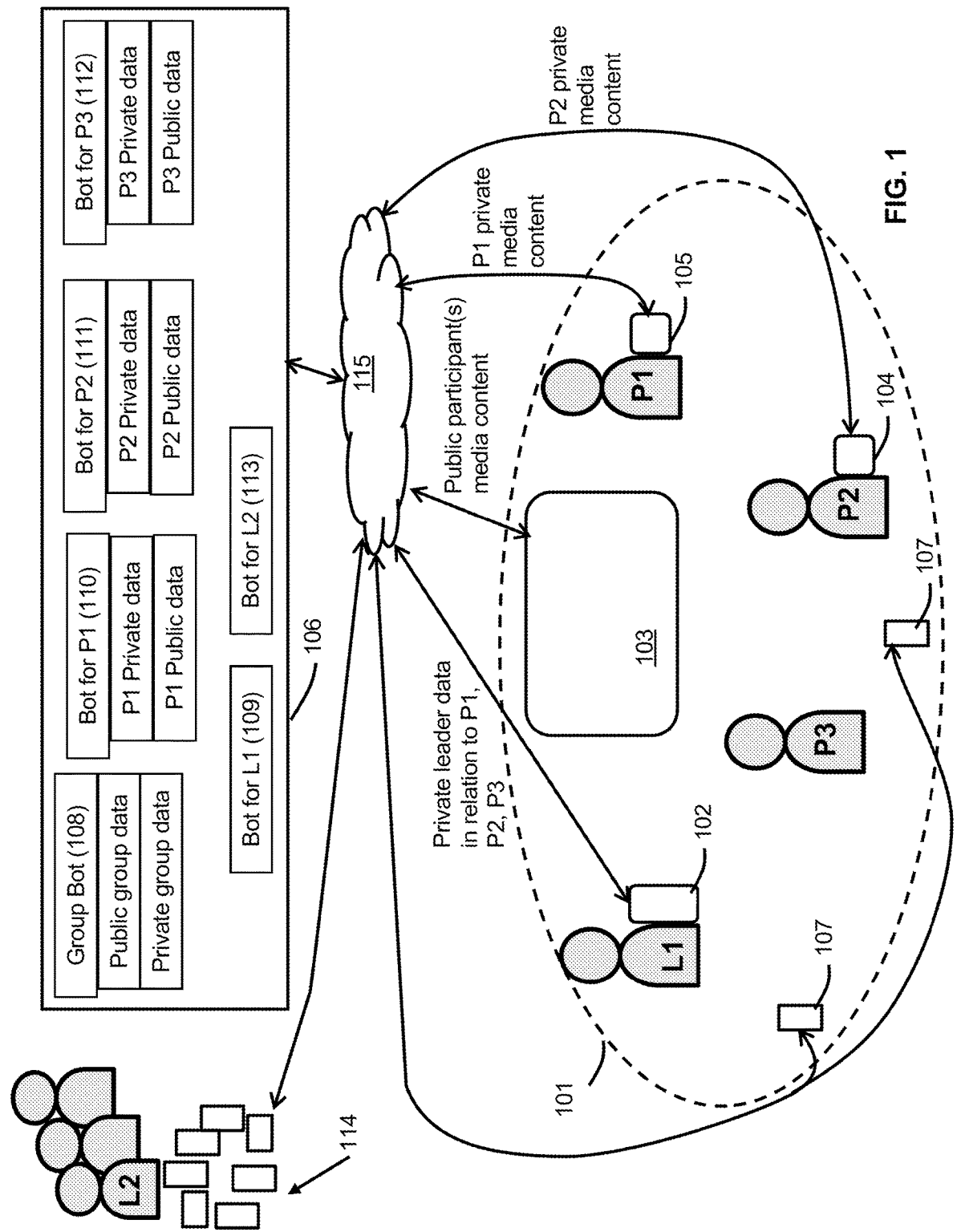
FIG. 1 is a schematic diagram of an example of a computing system and multiple devices interacting with each other to assist in group sessions.

It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It is herein recognized that there is a desire for a personalized and, yet scalable, solution to assist people participating in group therapy sessions and to assist group leaders. In an example aspect, this assistance includes specifically helping the group leaders to manage disruptive behaviors and agitated moods of group participants. In another example aspect, this assistance includes helping group leaders to engage group participants who are withdrawn (e.g. quiet and non-participatory). In another example aspect, this assistance includes an assistive device detecting the behavior or mood of a group participant and automatically engaging them with personalized digital content. In another example aspect, this assistance includes helping group leaders to record notes, suggestions and observations, and, in a further example aspect, to distribute those notes to other relevant users (e.g. other group leaders, caregivers, physicians, etc.).

It will be understood that while the examples herein relate to a group leader interacting with participants in a group session, these computing processes and computing systems described herein can also be used to assist an individual (e.g. a caregiver, a physician, a coordinator, a group leader, a trainer, a teacher, etc.) to interact with another individual (e.g. a patient, a senior, a person receiving help, a trainee, a student, etc.). In other words, the computing systems and computing processes described herein can also be used for one-to-one interactions between two people.

The terms group leader, leader, caregiver, coordinator, teacher, trainer, and helper are herein used interchangeably.

The terms group participant, participant, patient, loved one, senior, student and trainee are herein used interchangeably.

Turning to FIG. 1, is an example embodiment of assistive computing devices used to assist a group of people 101, which can be used during the group session. In this example, there is a leader L1 and participants P1, P2 and P3.

The leader L1 has a user device 102. Non-limiting examples of the leader's user device include a mobile device, a smartphone, a laptop, a tablet computer, a smartwatch, and a wearable device with audio output or visual output (or both). In an example embodiment, the leader's user device 102 includes one or more sensors to receive the leader's input. For example, the user device 102 includes a microphone to receive voice input. Other examples of sensors include one or more of: a touch-sensitive display device, buttons, gyroscopes, accelerometers, sensors to detect brain signals, sensors to detect muscle signals, sensors to detect silent speech (e.g. silent speech interface), and a camera device.

For example, in addition or in alternative to audible voice input, the leader can use other ways (e.g. silent speech, actions, facial expressions, lip movement, typing, touch interface, whispering) to quietly interact with the software to make notes or give commands, or both, so that other people in the local vicinity cannot hear the leader's input. These types of quiet user interactions can also be used to activate the private mode or the public mode.

The participant P2 has their own user device 104 and the participant P1 has their own user device 105. Non-limiting examples of the user devices 104, 105 include a mobile device, a smartwatch, a smartphone, a laptop, a tablet computer, and a wearable device with audio output or visual output (or both). In an example embodiment, each of these user devices include one or more sensors to receive the leader's input. For example, the user device 102 includes a microphone to receive voice input. Other examples of sensors include one or more of: a touch-sensitive display device, a button, a gyroscope, an accelerometer, a sensor to detect brain signals, a sensor to detect muscle signals, a sensor to detect silent speech (e.g. silent speech interface), a sensor to detect pulse or heart rate, a sensors to detect blood pressure, and a camera device. In an example embodiment, the user device for a participant is a combination of devices, such as a hearing aid or audio-headset that is paired to a smartwatch or a smartphone.

In some example embodiments, participants do not require their own user device. For example, P3 does not have their own user device. However, private content specific to the participant P3 can be served to him/her via the leader, or via the leader's personal device 102. As will be discussed below, public content specific to P3 or public content for the entire group can be served (e.g. outputted by visual display or audio speakers) through the group output device 103.

In the local vicinity of the group (e.g. in the same space, in the same room, etc.), there is a group output device 103. This group output device 103, for example, includes a visual display device or an audio output device, or both. For example, the group output device is a large display screen (e.g. such as a smart TV or a flat-screen monitor). In another example, the group output device is a multimedia projector that projects light images on to a screen. In this way, the group can easily see the images or hear the sounds, or both. In an example embodiment, the group output device also includes input devices, such as a camera or a microphone, or both, or is in data communication with one or more of these input devices.

In an example embodiment, there are external IoT devices 107 located within the same local vicinity (e.g. in the same space, in the same room, etc.) that can monitor audio and visual data of the group. For example, the IoT devices 107 include a microphone to detect what people are saying or a camera to see what people are doing, or both. In a further example aspect, these same devices have audio speakers to output sound.

In an example embodiment, all the leader and the participants are in the same location. In another example embodiment, the leader is remotely located and is able to interact with the participants through the group output device 103, or a personal device on a participant (e.g. user device 104, 105), or both. In another example embodiment, one or more of the participants are remotely located and are able to participate with the leader and other group participants using their user device (e.g. user device 104, 105).

The system also includes a server computing system 106, also herein called the data enablement platform 106, which interacts with the devices 102, 103, 104, 105 and 107 over a data network 115 (e.g. the Internet or a private network, or a combination of both).

The data enablement platform 106 also interacts with other computing devices 114 via the data network 115. For example, one or more of these devices are other user devices of other leaders (e.g. leader L2), administrators, family members, friends, etc. In an example embodiment, these other computing devices 114 could include one more different IoT devices that interact with participants or the leaders, or both.

In an example embodiment, a leader L2 receives the data from the group session lead by L1, and the leader L2 can use this information to prepare another group session or for personal one-to-one interactions with one or more of the participants.

The data enablement platform 106 includes one or more server machines that stores and executes computing processes and data for one or more group bots 108, one or more bots for leaders 109, 113, and one or more bots for participants 110, 111, 112.

It will be appreciated that the term "bot" is known in computing software and computing intelligence to mean a software robot or a software agent. In an example aspect, the bots described herein have machine learning capability.

For example, there are different group bots 108 for different purposes. For example, there is a group bot specific to a physical exercise activity; there is a group bot specific to brain exercise activity; there is a group bot to learn cooking; there is a group bot for meditation; there is a group bot for making music or enjoying music; there is group bot to learn a craft or to do a craft; there is a group bot for family counseling; there is a group bot for end-of-life counseling; there are group bots for different types of counseling; there is a group bot to learn about a topic; there is a group bot to learn a skill; there is a group bot to share personal challenges; etc.

It will be appreciated that different group bots, for example, have data content that is specific to the purpose of the group session. In a further example aspect, different group bots have different user-interaction modes that is specific to the purpose of the group session. For example, the user-interaction can vary amongst the group bots by: volume of the audio data; type of language (e.g. type of words selected) when giving suggestions and response; type of sentence structure; type of sentence structures; speed of audio voice; cadence of audio voice; tonality of audio voice; timing of when suggestions or responses (or both) are provided; etc.

For example, a group bot for yoga activity includes data specific to yoga (e.g. yoga demonstration videos, yoga audio content, relaxing music, etc.). The group bot specific to yoga also presents messages (e.g. audio messages, images, text, video messages, etc.) to the leader, or the participants, or the entire group in a relaxing manner (e.g. quieter audio voice, slower pace of speaking, choice of calmer words, etc.) that reflects the yoga group session. The group bot specific to yoga also includes software intelligence to give suggestions specific to the leader or the specific participants, or the entire group, that is pertinent to the yoga activity (e.g. suggestions for a leader to demonstrate better yoga positions for the given participants, suggestions to help a participant calm their mind, etc.).

In another example, a group bot for country dancing includes data specific to country dancing (e.g. country dancing demonstration videos, country dance music, instructional audio, etc.). The group bot specific to the country dancing also presents messages (e.g. audio messages, images, text, video messages, etc.) to the leader, or specific participants, or the entire group in an upbeat manner that reflects the country dancing session. For example, the messages are presented in a louder audio voice, with faster speaking cadence, and more cheerful (e.g. higher pitched) tonality. The messages are automatically composed with words that is considered upbeat and cheerful. The group bot specific to country dancing also includes software intelligence to give suggestions specific to the leader or specific to the participants, or suggestions that apply to the entire group, that is pertinent to country dancing (e.g. suggestions for a leader to demonstrate country dance steps for the given participants, suggestions to help a participant have fun while dancing, etc.).

In another example embodiment, there is only one type of group bot which is used across various different group scenarios.

In a further example aspect, there is bot for each participant. For example, there is bot 110 for the participant P1, there is a bot 111 for the participant P2, and there is a bot 112 for the participant P3.

There is also a bot for each leader. In this example, there is a bot 109 for the leader L1 and a bot 113 for the leader L2.

In a group session, a group bot 108 interacts with a leader bot and one or more participant bots. For example, during the group session 101, the group bot 108 interacts (e.g. transmits and receives data) with the L1's leader bot 109 and the bots 110, 111, 112 for the participants P1, P2, P3.

It will also be understood that each bot has access to public data and private data, and that each bot will, under certain conditions (e.g. detected circumstances of a person, privacy permissions, permissioned device(s), etc.) send public data or send private data, or in some conditions both types of public data and private data.

For example, a group bot 108 has access to public group data and private group data.

In this example, the bot for P1 110 has access to private data and public data associated with P1. The bot for P2 111 has access to private data and public data associated with P2. The bot for P3 112 has access to private data and public data associated with P3.

In an example aspect, P1's device 105 is permissioned to output P1 private data associated with the bot 110 for P1. In an example aspect, the leader device 102 is also permissioned to output P1 private data associated with the bot 110 for P1. However, the other devices like the group output device 103 and P2's device 104 are not permissioned (in other words, restricted) for outputting the P1 private data.

In an example aspect, P1's device 105 is permissioned to output P1 private data associated with the bot 110 for P1. In an example aspect, the leader device 102 is also permissioned to output P1 private data associated with the bot 110 for P1. However, the other devices like the group output device 103 and P2's device 104 are not permissioned (in other words, restricted) for outputting the P1 private data. However, the group output device 103 is permissioned to output the P1 public data.

Similarly, in an example aspect, P2's device 104 is permissioned to output P2 private data associated with the bot 111 for P2. In an example aspect, the leader device 102 is also permissioned to output P2 private data associated with the bot 111 for P2. However, the other devices like the group output device 103 and P1's device 105 are not permissioned (in other words, restricted) for outputting the P2 private data. The group output device 103 is permissioned to output the P2 public data.

In another example aspect, the term "public group data" herein refers to data content that is for all group participants to watch, hear, or read, or a combination thereof.

The term "private group data" herein refers to data content that is about the overall group (e.g. session specific, people specific, feedback, future suggestions, etc.) and that is for the group leader or group leaders (e.g. L1, L2) to see. This type of private group data is analytical data, summary data, suggestion data, feedback data, etc. This type of private group data is, for example, specific to one or more members of the group; specific to certain activities or comments or content of a given group session; specific to overall group; specific to one or more group leaders; etc. In other words, the private group data is not for the group participants (e.g. P1, P2, P3) to see or hear or both. In an example aspect, the private group data can be shared with others (e.g. other administrators, coordinators, directors, etc.) as determined according to a permission setting.

Private data for a participant herein refers to personal data that is specific to a given group participant. This private data is not outputted in group output devices (e.g. device 103), as it is intended only for the given group participant. For example, a participant's personal data can include one or more of: data that is sent or created by family for the participant; data that is sent or created by friends for the participant; data that is sent or created by the participant for themselves or for others, or both; their medical data; their physical activity data; their personal comments or thoughts data; their biological data; their preferred media content data; etc. The private data of a participant is not displayed or outputted on a group output device 103 for all to see or hear (or both). Instead the private data of a given participant is outputted on a permissioned device associated with or belonging to the given participant. For example, private data of the participant P1 is outputted onto the P1's user device 105. In another example, private data of the participant P2 is outputted onto P2's user device 104. In another example, private data of the participant P3 is outputted onto the leader L2's user device 102, so that the leader L2 can use their device 102 to show the participant P3 (e.g. without showing the other participants P1 and P2).

Public data for a participant herein refers to data that is specific to a given group participant, and that has been permissioned to be outputted (e.g. visually or via audio, or both) in front of other group participants. In other words, public data for a given participant (e.g. for P1) can be shown over the group output device 103, meaning that the participants P1, P2 and P3 could all see this public data being displayed.

More generally, public data for a participant can be served on group output device 103. By contrast, private participant data is served on the given participant's device or the private participant data is served to the leader's user device. For example, the leader can relay or use the private content of a given participant, or the leader can show the private data to the given participant on their leader's user device.

During a given group session, the leader bot for L1 109 interacts with the group bot 108. The group bot 108 also interacts with the bots of the participants in the group session (e.g. bot for P1 110, bot for P2 111, and bot for P3 112). In other words, in the example shown in FIG. 1, multiple bots are active during this given group session.

In an example aspect, a given bot for a given participant (e.g. bot 110 for P1) outputs data to interact with the given participant independently from the group bot 108.

In another example aspect, the given bot (e.g. bot 110) for the given participant is prompted by the group bot 108 to output data to interact with the given participant. In other words, the group bot 108 and the given bot of the given participant interact with each other to provide coordinated data output to the given participant.

In a further example aspect, a given leader bot of a given leader (e.g. leader bot 109 for L1) interacts with the group bot 108. For example, the group bot 108 sends data to the leader bot 109, and the given leader bot (e.g. bot 109) in turn outputs data to the given leader (e.g. L1). In another example, the given leader bot (e.g. bot 109) receives input data from the given leader, which in turn is sent to the group bot 108; and the group bot 108 uses this input data to trigger an action (e.g. record a note; record feedback; search for a relevant suggestion; send a command or data to one or more of the bots 110, 111, 112 of the participants; etc.).

It will be appreciated that the bots described herein can interact with each other and in different ways according to various example embodiments.

In an example aspect, a bot for a participant or a bot for a leader, or both, applies machine learning to identify unique data features in the user voice. Machine learning can include, deep learning. Currently known and future known algorithms for extracting voice features are applicable to the principles described herein. Non-limiting examples of voice data features, also herein called audio voice attributes, include one or more of: tone, frequency (e.g. also called timbre), loudness, rate at which a word or phrase is said (e.g. also called tempo), phonetic pronunciation, lexicon (e.g. choice of words), syntax (e.g. choice of sentence structure), articulation (e.g. clarity of pronunciation), rhythm (e.g. patterns of long and short syllables), melody (e.g. ups and downs in voice), vowel duration, peak vocal sound pressure (e.g. measured in SPL), continuity of phonation, tremor, pitch variability, and loudness variability. As noted above, these data features or audio voice attributes can be used to identify behaviors and meanings of the user (e.g. a participant or a leader, or both), and to predict the content, behavior and meaning of the user in the future. It will be appreciated that prediction operations in machine learning include computing data values that represent certain predicted features (e.g. related to content, behavior, meaning, action, etc.) with corresponding likelihood values.

In another example aspect, in a one-to-one scenario between a leader and a participant, the group bot may be activated or may not be activated. In other words, in an example embodiment of a one-to-one scenario, only a leader bot and a bot for a given participant are used to interact with each other.

In another example embodiment of a one-to-one scenario, the group bot can be activated. For example, the group bot provides content and interaction media that may not be available via the bot for the given participant. In another example, the leader takes notes about the given participant in a one-to-one scenario, which are provided to a group bot, so that the group bot is able to later cater interaction to the given participant in future group scenarios when the given participant is present.

Figure 2:
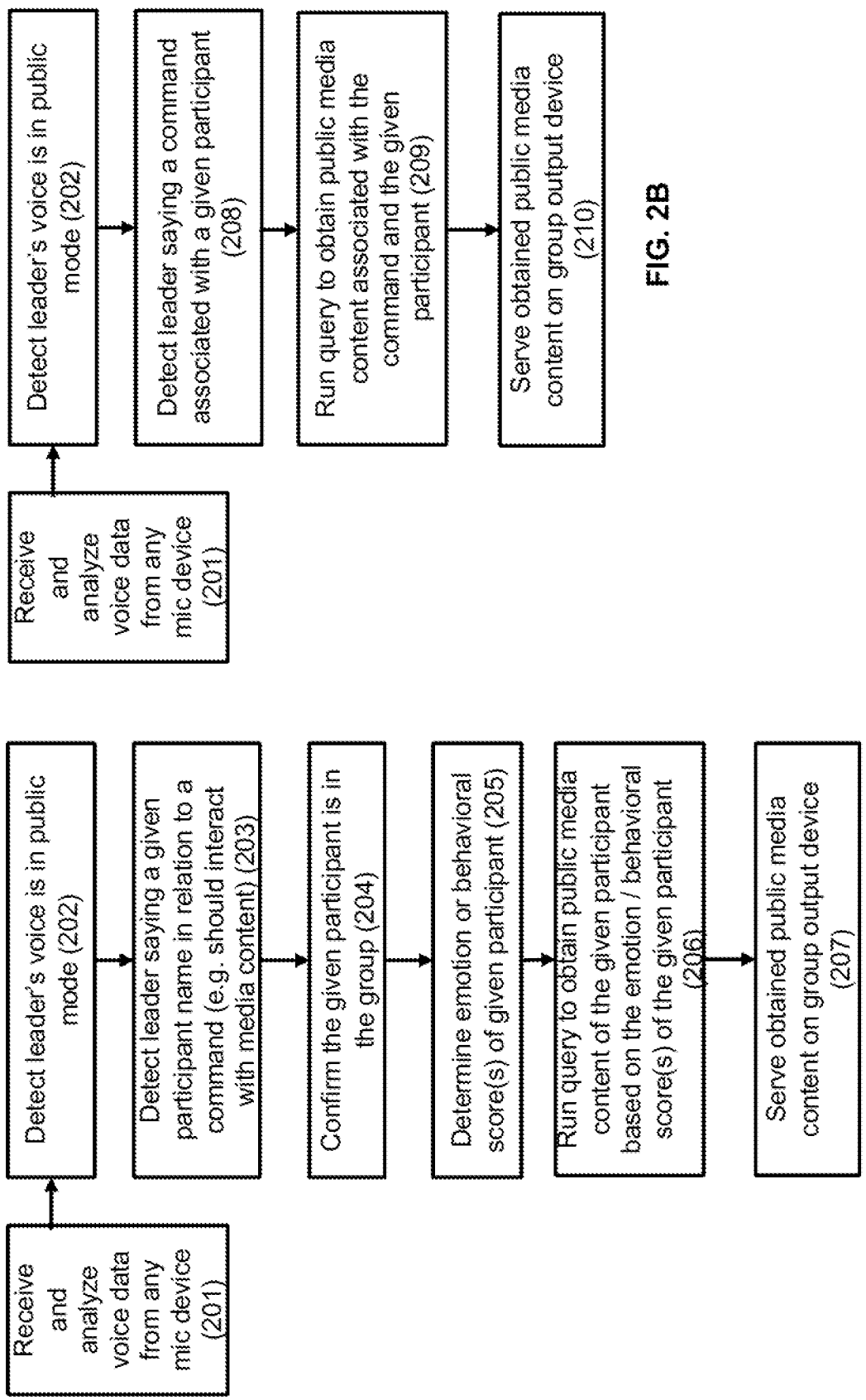
FIG. 2A is a flow diagram of example computer executable or processor implemented instructions for a leader initiating the computing system to publicly serve media content via a group output device to a given participant in the group session.
FIG. 2B is a flow diagram similar to FIG. 2A, but according to a different example embodiment.
Figure 3:
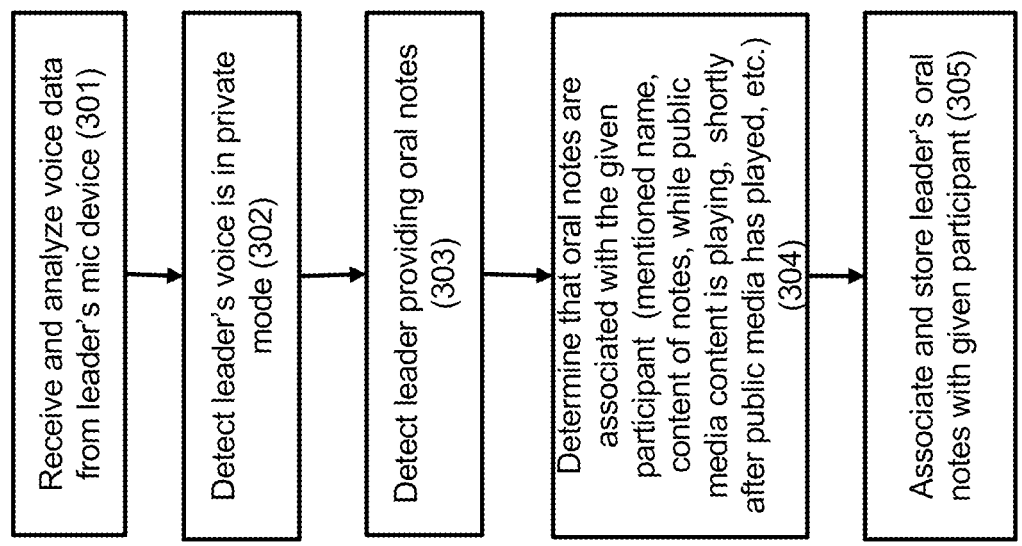
FIG. 3 is a flow diagram of example computer executable or processor implemented instructions for recording oral notes in a private mode, as determined by the leader's voice data.

Turning to FIGS. 2 and 3, example computer executable instructions are provided for determining the mode of a bot based on a leader's voice. For example, in FIG. 2, the leader's voice is analyzed to indicate that one or more bots are to be used in a public mode. In FIG. 3, the leader's voice is analyzed to indicated that one or more bots are to be used in a private mode.

In FIG. 2A, a computing device (e.g. the leader's own user device 102) or some other computing device with a microphone that is in proximity of the group session 101 is used to receive and analyze the voice data, which is recorded by a given microphone (block 201). Part of the analysis includes computing a speech-to-text process, to identify the text or words of the detected voice data.

The computing device that recorded the audio data (e.g. a user device or edge device in proximity of the group session), or a cloud computing device that is part of the data enablement platform, or both, is used to detect that the leader's voice is in a public mode (block 202).

For example, the leader's voice is determined to be in a public mode based on comparing the audio values of different parameters and comparing them with various threshold values. These different parameters of the voice include, for example, one or more of the following: volume of the voice, tonality of the voice, sound frequency of the voice, etc.

For example, if the volume of the detected voice is above a certain threshold value, then the voice command indicates a public mode and that public data is to be accessed, created, modified, etc. By contrast, along the same example, if the volume of the detected voice is below the certain threshold value, then the voice command indicates a private mode and that indicates that private data is to be accessed, created, modified, etc. In one example, the detected voice parameters alone are used to determine a public mode or a private mode. In another example, a combination of the detected text (resulting from the speech-to-text) and the detected voice parameters are used to determine a public mode or a private mode. For example, when the leader whispers a command to start the private mode (e.g. whispers "private mode"), then the private mode is activated.

In an alternative example, the text resulting from the speech-to-text processing is analyzed. If the leader is detected to say a certain set of keywords, then the public mode is activated (e.g. saying "Public Mode"). To activate private mode, the leader says "Private Mode", or says "Private Mode" followed by a password. Other security features or parameters can be combined to when verifying or launching the private mode, such as the leader already being logged into the application or device.

As noted above, other parameters, either in combination or in alternative, can be used to automatically determine whether the leader is speaking in a public mode or in a private mode.

At block 203, as part of analyzing the voice data, the leader is detected to have said a given participant name in relation to a command. For example, the given participant's name is "Bob" and the voice data includes the leader having said something like: "Bob, look at the screen"; "Look at the screen, Bob"; or "Bob, listen to the speaker". It will be appreciated that there are many other voice commands that could be given.

At block 204, after detecting the participant name, the computing system confirms that the detected participant name is in the group session. For example, participants or a group leader manually or semi-automatically confirm attendance of the participants in the group session. The computing system compares the detected participant name against the list of participants that are presently in attendance in the group session.

After confirming that the detected participant name is in attendance in the group session, at block 205, the computing system determines the emotion or behavior score(s) of the given participant. For example, this can be done by querying a table that stores the emotional states or behavioral scores of participants. It will also be appreciated that there are many different ways to ascribe an emotional state or behavioral score (or both) to a person. For example, this can be done automatically, manually, or semi-automatically.

At block 206, the computing system runs a query to obtain public media of the given participant based on the obtained emotional state or behavioral score(s) of the given participant. For example, if Bob's behavioral score or emotional state indicate he is an angry state, then a calming video that is associated with Bob's public data (e.g. a fishing video on the lake, which Bob likes) will automatically be obtained and played.

More generally, at block 207, the computing system serves the obtained public media content on the group output device 103.

It will be appreciated that the emotional states or behavior scores used in the above computations are especially applicable to group sessions in which emotions and behaviors are of consideration. In other examples, other types of scores or parameters are used to select the media content. For example, in an education setting, a learning score or an interest score is used to select the appropriate media content for a group participant. In another example, in a sports training setting, a physicality score or an agility score or a technique score, or the like, is used to select the appropriate media content for a group participant.

In FIG. 2B, a different example embodiment is shown in which a leader speaks in a public manner to trigger the playing of media content for a particular participant, and the media content is shown on the group output device.

Turning to FIG. 2B, blocks 201 and 202 are executed, which are the same as the blocks described with respect to the embodiment in FIG. 2A.

For example, the leader speaks or says "Bob's happy video" or "Bob's favorite video", and the computing system uses speech-to-text processing to identify the text of this voice data. At block 208, the computing system detects that the leader has said a command associated with a given participant (e.g. Bob). This could be a simple look-up, in which the text data (which has been obtained from the voice data) is used to match a pre-stored command.

At block 209, after identifying the command the computing system runs a query to identify the public media content associated with the command and the given participant.

At block 210, the obtained public media content is served (e.g. displayed) on the group output device 103. For example, Bob's public data includes a video of people surfing. Based on the leader's spoken voice data (e.g. "Bob's happy video" or "Bob's favorite video"), which has been determined to be in a public mode, then the computing system causes the video of people surfing to be shown on the group output device.

Turning to FIG. 3, an example embodiment of computer executable instructions is provided for detecting that a leader's voice is in a private mode, and subsequently the computing system interacting with the leader in a private manner to create, read, update and delete data. For example, if the leader L1 interacts with their device 102 using a private voice, then the following interactions with the computing system 106 are in a private manner (e.g. affecting private group data associated with the group bot 108, or other private data associated with any of the participants). In the particular example of FIG. 3, the leader privately makes oral notes, which are stored as private data in association with the group bot 108.

At block 301, the mic of the leader own device 102 detects voice data, and this voice data is analyzed locally on the device 102 or on the computing system 106, or a combination of both. This analysis, for example, includes speech-to-text processing to output text from the voice data.

At block 302, as part of the analysis, the computing system (e.g. either the device 102 or the data enablement platform 106, or both) determines that the leader's voice is in a private mode.

For example, the leader's voice is determined to be in a private mode based on comparing the audio values of different parameters and comparing them with various threshold values. These different parameters of the voice include, for example, one or more of the following: volume of the voice, tonality of the voice, sound frequency of the voice, etc. An example is provided above with respect to block 202. In particular, the audio characteristics of a person whispering or speaking quietly (e.g. herein used to indicate a private mode), are very different from the audio characteristics of a person speaking loudly or conversationally for all to hear (e.g. herein used to indicate a public mode).

In an example embodiment, the leader whispers the following, as detected by the microphone: "Take note about Bob. He is feeling very angry today. After I spoke to him about surfing, he cheered up. Suggestion is that we learn more about surfing to better connect with Bob."

At block 303, the computing system detects that the leader is providing oral notes. For example, this detection is based on the text "take note".

At block 304, the computing system determines that the oral notes are associated with the given participant. For example, the computing system detects the participant name has been mentioned (e.g. "Bob") in relation to the note, and therefore associates the oral notes (e.g. the text version of the voice data) with Bob in the data enablement platform 106.

In another example, the computing system automatically detects that the content of the oral notes relates to one or more characteristics of a given participant and therefore associates the oral notes (e.g. the text version of the voice data) with that given participant. For example, the oral note is "He is responding very well after his surfing video played", and the computing system identifies a man from the word "He" and that the man is Bob since the surfing video is associated with Bob; therefore, the oral notes are associated with Bob. Other methods of automatically associating an oral note with a given participant include: (1) detecting that the oral note from the leader is said while media content associated with the given participant is playing, and then associating that oral note with that given participant; and (2) detecting that the oral note from the leader is said shortly after the media content associated with the given participant has finished playing (e.g. said within x seconds of the media content finishing), and then associating that oral note with that given participant. It will be appreciated that there are various approaches to automatically associating oral notes with a given participant In other example embodiment, the leader manually associates the oral notes with a given participant, for example, via a touch screen graphical user interface (GUI) or some other interface.

After the association has been made, at block 305, the leader's oral notes are stored in association with the given participant. The oral notes (e.g. text version of the voice data) is stored as private data associated with the participant's bot, or as private data associated with the group bot, or both. In an example where there is another leader (e.g. leader L2) associated with the group, then that other leader L2 can access the leader L1's oral notes about Bob. In this way, the leader L2 can benefit from the knowledge, suggestions, etc. about the leader L1's interaction with Bob.

Figure 4A:
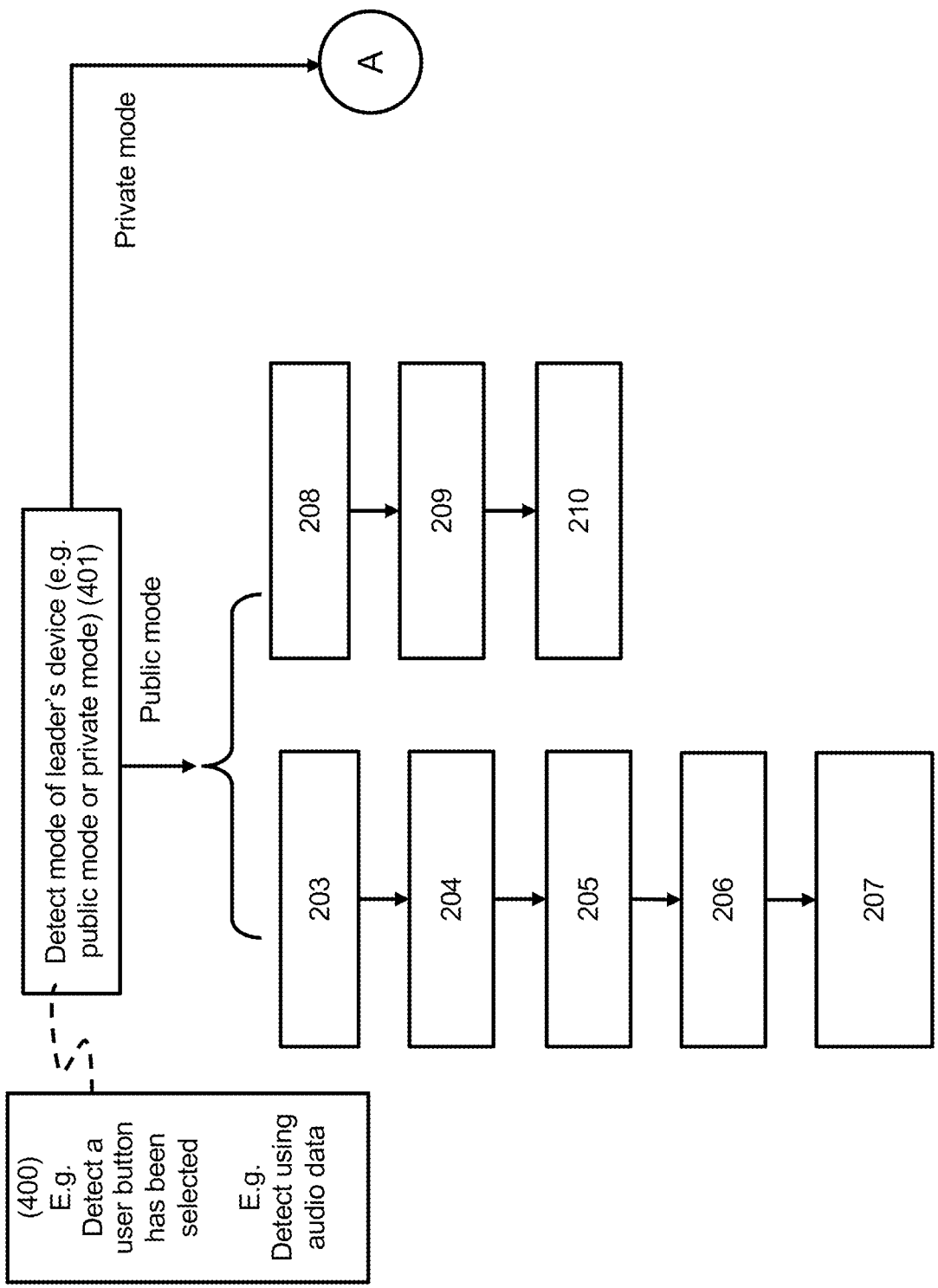
FIGS. 4A and 4B is a flow diagram of example computer executable or processor implemented instructions for detecting a private mode or a public mode of the leader's device and taking action according to the context of the private mode or the public mode.
Figure 4B:
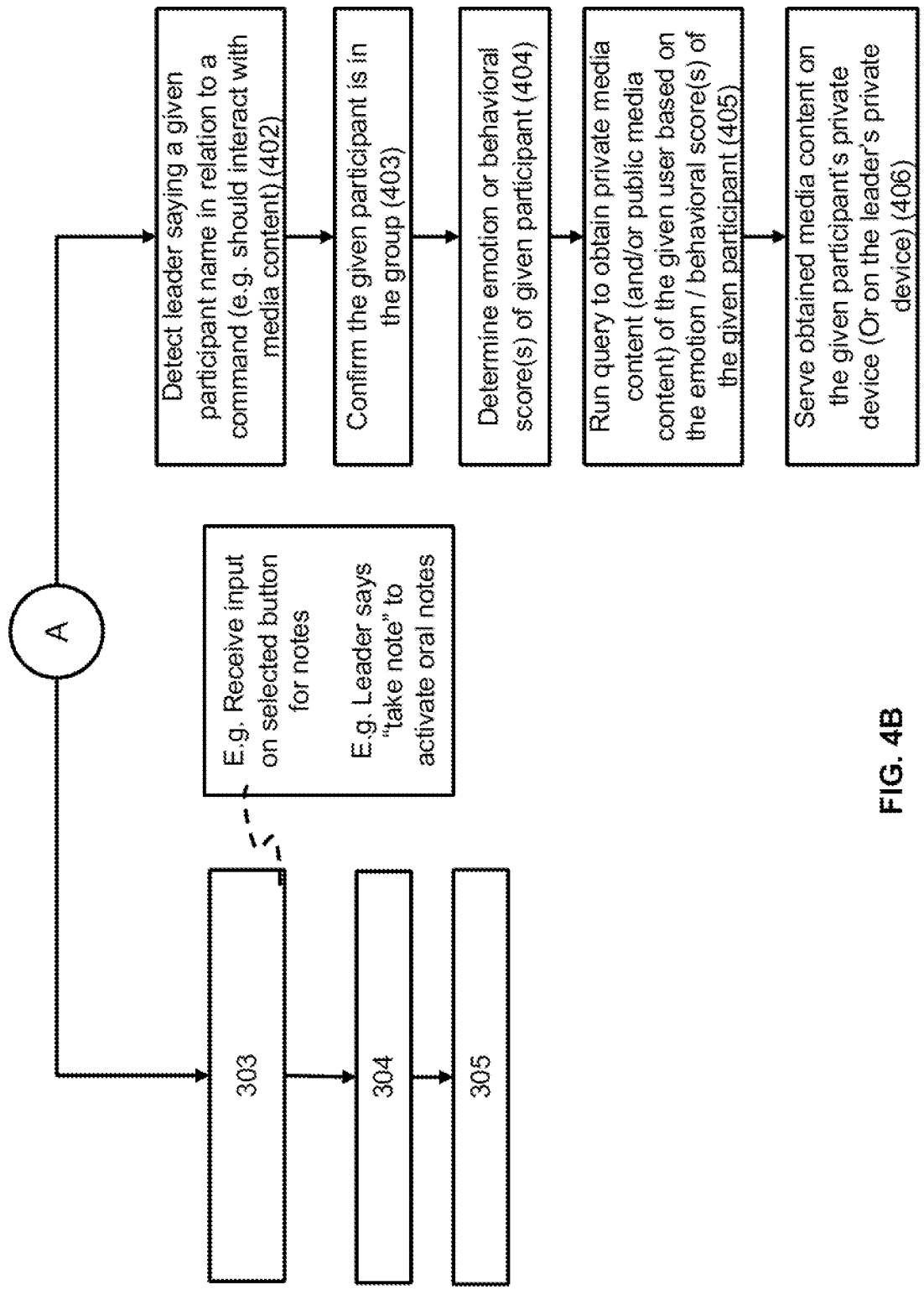

Turning to FIG. 4A and FIG. 4B, another example embodiment is provided for a leader to interact with the data enablement platform in a public mode or a private mode.

At block 401, the leader's device 102 or the data enablement platform 106, or both, detects the public mode or the private mode the leader's device. For example, this can be done by the leader selecting a button on a touch screen GUI indicating that the leader's device is in a private mode, or in a public mode (block 400).

In another example, this determination is made using audio data. For example, the leader can say "private mode" to trigger the private mode, and the voice data is subsequently processed in a private mode. By default, when the user does not say "private mode", then the leader's device is in a public mode; accordingly, the leader's voice data is processed in the public mode by default.

In another example, the determination of private mode and the public mode is made by audio characteristics, including and not limited to volume, tonality, sound frequency, etc. For example, the leader may whisper a command and the audio characteristics of a whisper are used to automatically determine that the leader is interacting in a private mode.

In the public mode, the operations of blocks 203 to 207 are executed according to an example embodiment.

In the public mode, according to another example embodiment, the operations of blocks 208 to 210 are executed.

In the private mode, the process is shown in more detailed in FIG. 4B, continuing from the "A" reference shown in FIG. 4A.

Turning to FIG. 4B, in an example embodiment of the private mode, the leader orally makes notes according to the operations of blocks 303, 304 and 305. In an example embodiment, as part of block 303, the leader's device receives an input on a selected button (e.g. a button on a touch screen GUI) to indicate that the leader is taking notes. Alternatively, for example, the leader says "take note" or the like to indicate the note taking mode.

In another example embodiment of the private mode, the leader is detected saying "Bob looks sad; play something that will cheer Bob". More generally, at block 402, the leader is detected saying a given participant name in relation to a command.

At block 403, the group bot confirms that the given participant name is in the group.

At block 404, the data enablement platform determines the emotional state or behavioral score of the given participant. In an example embodiment, the leader defines the emotional state or defines the behavioral score (e.g. Bob looks sad). This determination can be made in other ways, such as querying a database that stores the emotional state or behavioral scores of the participant.

At block 405, the data enablement platform runs a query to obtain private media content, or public media content, or both, that is associated with the given participant based on their emotional state or behavioral score. For example, the data enablement platform obtains cheerful media content from private data associated with Bob's bot, or obtains cheerful media content from public data associated with Bob's bot, or both.

In an example embodiment, as the leader is invoking the command in a private mode, the private media content for Bob is queried and served to Bob.

At block 406, the data enablement platform serves the obtained media content on the given participant's private device (e.g. Bob's private device intended for Bob's consumption only). Alternatively, the obtained media content is served on the leader's private device and the leader shows their private device to Bob for Bob to see or hear, or both.

Figure 5:
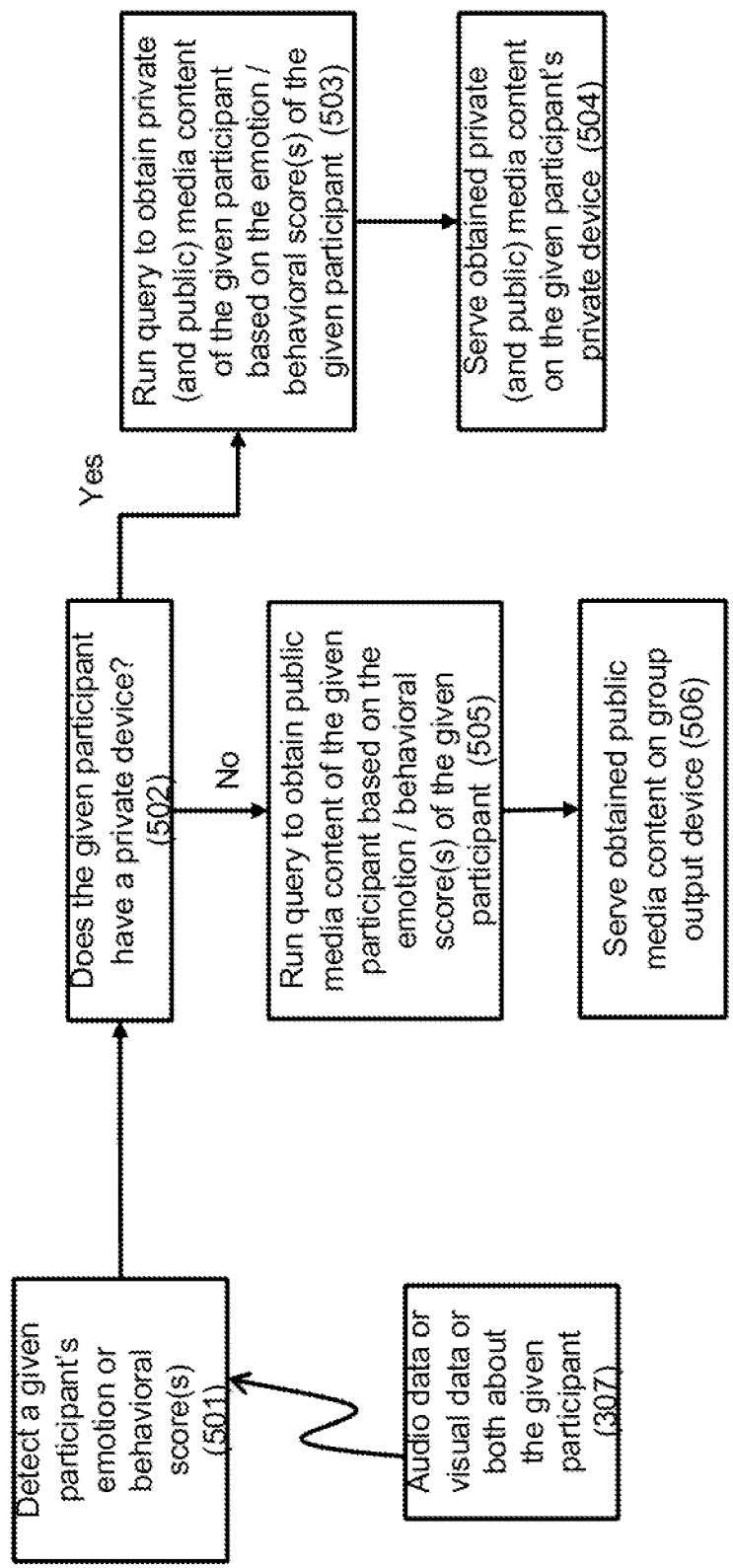
FIG. 5 is a flow diagram of example computer executable or processor implemented instructions for a given participant in a group session initiating the computing system to serve media content via an output device.

Turning to FIG. 5, an example embodiment is shown for a participant interacting with the data enablement platform 106 during a group session.

At block 501, the data enablement platform 106 detects a given participant's emotional state or behavioral score. This can be done in one or more ways. Examples include: the leader providing an indication of the emotional state; detecting the emotion or behavior of the given participant based on recorded audio data (e.g. what they say, how they say it, etc.); detecting the emotion or the behavior of the given participant based on recorded visual data (e.g. their body posture, their facial expression, their movements, etc.); detecting the emotion or the behavior of the given participant based on recorded biological data (e.g. heart rate, blood pressure, body temperature, brain signals, muscle signals, etc.); and the given participant expressly indicating how they feel (e.g. touch screen selection indicating what they feel; they speak or say what they feel). Other approaches to detecting emotional state or behavioral score are applicable to the principles described herein.

At block 502, the data enablement platform determines whether the given participant has their own private device.

If so, at block 503, the data enablement platform runs a query to obtain private media content (e.g. private data) associated with the given participant's bot that is associated with the emotion or behavioral score of the given participant. For example, if the participant P1 is worried (e.g. the detected emotion or behavioral score), then private media content (e.g. a video) from a family member is selected the P1 private data of P1's bot 110; the video from the family member provides reassurance to the participant P1.

In another example embodiment, public media associated with P1's bot is obtained either in addition or in alternative to the private media.

At block 504, the obtained private media data or public media data, or both, is served to the given participant's private device (e.g. P1's private device 105).

At block 502, if the given participant does not have a private device, then the process continues to block 505. The data enablement platform runs a query to obtain public media content of the given participant based their emotion or behavioral score.

At block 506, this public media content (e.g. public data associated with P1's bot 110) is outputted via the group output device 103.

In this way, if the participant P1 has their own private device, private media or public media, or both, are outputted to P1 on their own device. On the other hand, if the participant P1 does not have their private device with them, then P1's private media is purposely not displayed or accessed and, instead, P1's public media is outputted on the group output device 103.

Figure 6B:
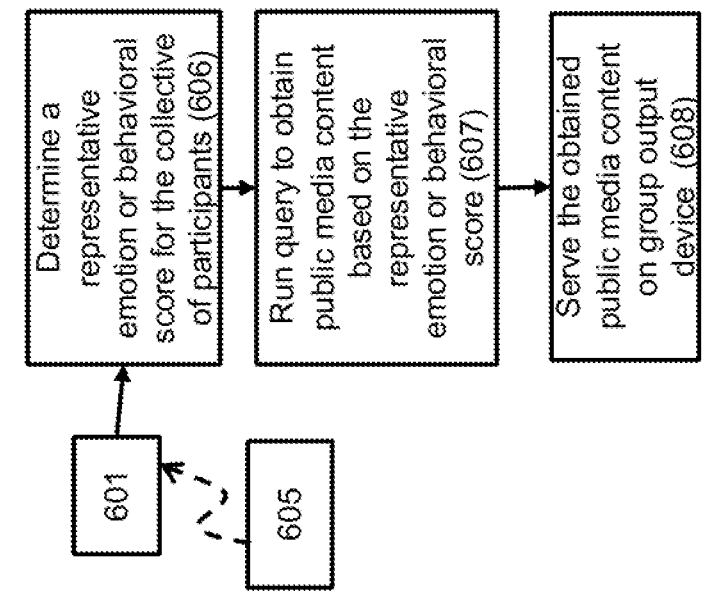
FIG. 6B is a flow diagram similar to FIG. 6A, but according to a different example embodiment.
Figure 6A:
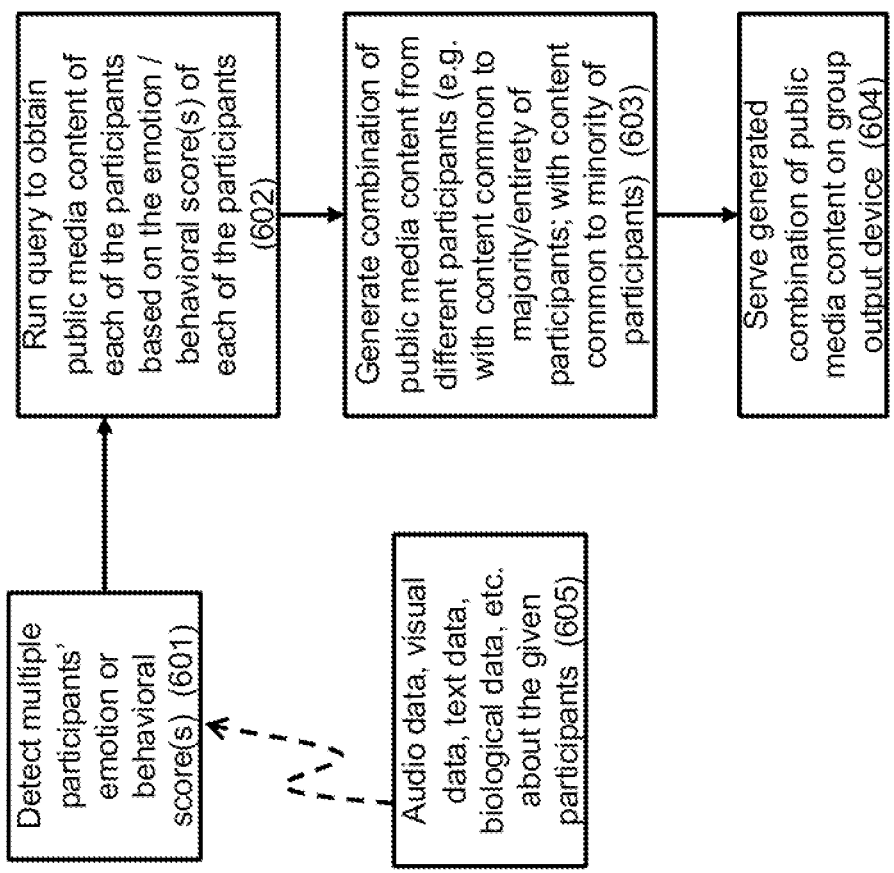
FIG. 6A is a flow diagram of example computer executable or processor implemented instructions for the computing system to automatically select and serve media content, via an output device, based on the multiple participants' emotion or behavioral scores in a group session.

Turning to FIG. 6A, an example embodiment of executable instructions is provided for outputting media content for the entire group of participants based on the collective emotions and behaviors of the participants.

At block 601, the data enablement platform detects multiple participants' emotions or behavioral scores. In an example embodiment, each of the bots for the participants computes an emotional state or behavior score for their respective participant. For example, this can be computed using various types of data including one or more of, audio data, visual data, text data, biological data, etc. (block 605).

At block 602, the data enablement platform runs queries to obtain public media content associated with each one of the participants, and further respectively based on the emotion or behavioral score of each one of the participants. For example, P1's public media associated with P1's bot 110 is obtained based on P1's emotion or behavior; P2's public media associated with P2's bot 111 is obtained based on P2's emotion or behavior; and P3's public media associated with P3's bot 112 is obtained based on P3's emotion or behavior.

At block 603, the data enablement platform generates a combination of this obtained public media content from the different participant. For example, the different content is queued in a play list. In another example, the different media content is recombined to generate a new media content file. For example, parts of P1 public media, parts of P2 public media, parts of P3 public media are played at different intervals.

In another example, a first public media file that is considered appealing to the majority and a second public media file that is considered appealing to the minority of the group are selected and queued.

At block 604, the selected public media file or files are outputted via the group output device. For example, the group bot outputs this public media data to the group output device.

FIG. 6B shows an alternative embodiment to FIG. 6A.

Turning to FIG. 6B, blocks 601 and 605 are executed. At block 606, the data enablement platform uses each of the emotional states or behavioral scores to determine a representative emotional state or a behavioral score for the collective of participants. For example, the representative emotional state or behavioral score is based on the highest number of participants having the same emotional state or behavioral score. In another example, the representative emotional state or behavioral score is based on taking the average or median, or some other statistical representation, of the multiple emotional states or behavioral scores.

At block 607, the data enablement platform runs a query to obtain public media content that is based on the representative emotional state or behavioral score associated with the entire group.

At block 608, the obtained public media content is served via the group output device.

Figure 7:
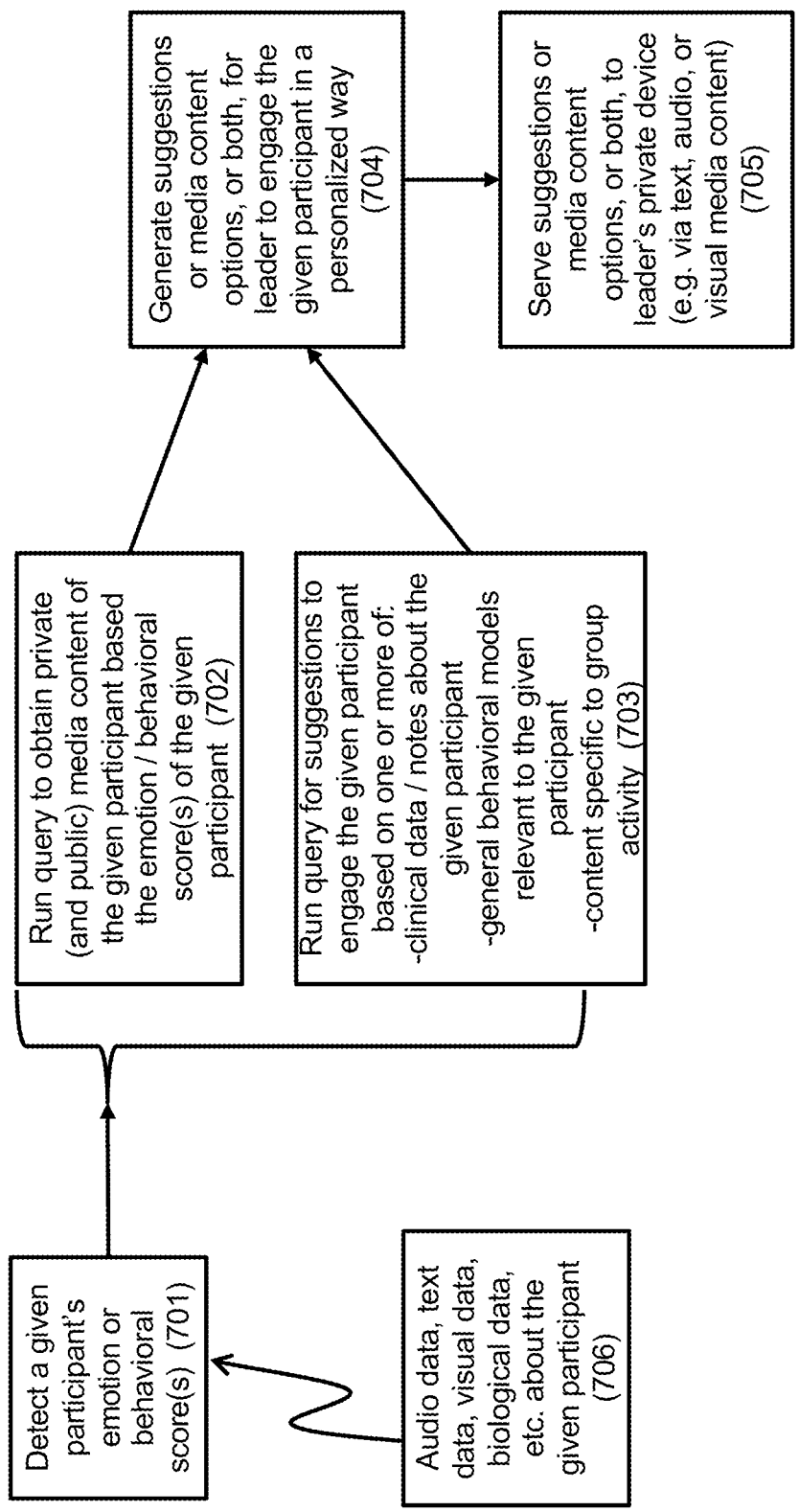
FIG. 7 is a flow diagram of example computer executable or processor implemented instructions for the computing system to generate and serve suggestions to a leader to engage a given participant in a group session.

Turning to FIG. 7, an example embodiment of computer executable instructions is provided for the data enablement platform 106 to provide suggestions to a leader about a given participant.

At block 701, a bot associated with a given participant (e.g. P1's bot 110) detects a given participant's emotional state or behavioral score. For example, this can be computed using various types of data including one or more of, audio data, visual data, text data, biological data, etc. (block 706).

At block 702, a bot associated with the given participant (e.g. P1's bot 110) runs a query to obtain private media content or public media content, or both, associated with the given participant based the emotional state or behavioral score of the given participant.

At block 703, the participant's bot or the group bot, or both, run a query for suggestions to engage the given participant. This query is based on one or more of: clinical data or notes about the given participant; general behavioral models associated with the given participant; content specific to the group activity or discussion; and their emotional state or behavioral score.

Pursuant to blocks 702 or 703, or both, at block 704, the group bot or the leader bot, or both, generates suggestions or options for media content, or both. These are generated for the leader to engage the given participant in a personalized way.

At block 705, the leader bot serves these one or more suggestions, or one or more media content options, or both, to the leader's private device.

For example, a suggestion is for the leader to discuss a certain topic with the given participant. In another example, a suggestion is to ask certain question to the given participant. In another example, a suggestion is to use certain examples or certain language with the given participant. In another example, a suggestion is to carry out a certain activity with the given participant. In another example, a suggestion is to play certain media content and ask certain questions in relation to the played media content. In another example, a suggestion is to shorten the discussion or activity with the given participant. In another example, a suggestion is to provide the participant certain materials or equipment. In another example, a suggestion is to communicate using stories. In another example, a suggestion is to provide more physical interaction, or to provide less physical interaction. It will be appreciated that other types of suggestions are applicable to the principles described herein.

In this way, the leader is provided with content and suggestions that are relevant, personal and likely to be effective to help the leader engage with the given participant.

Figure 8:
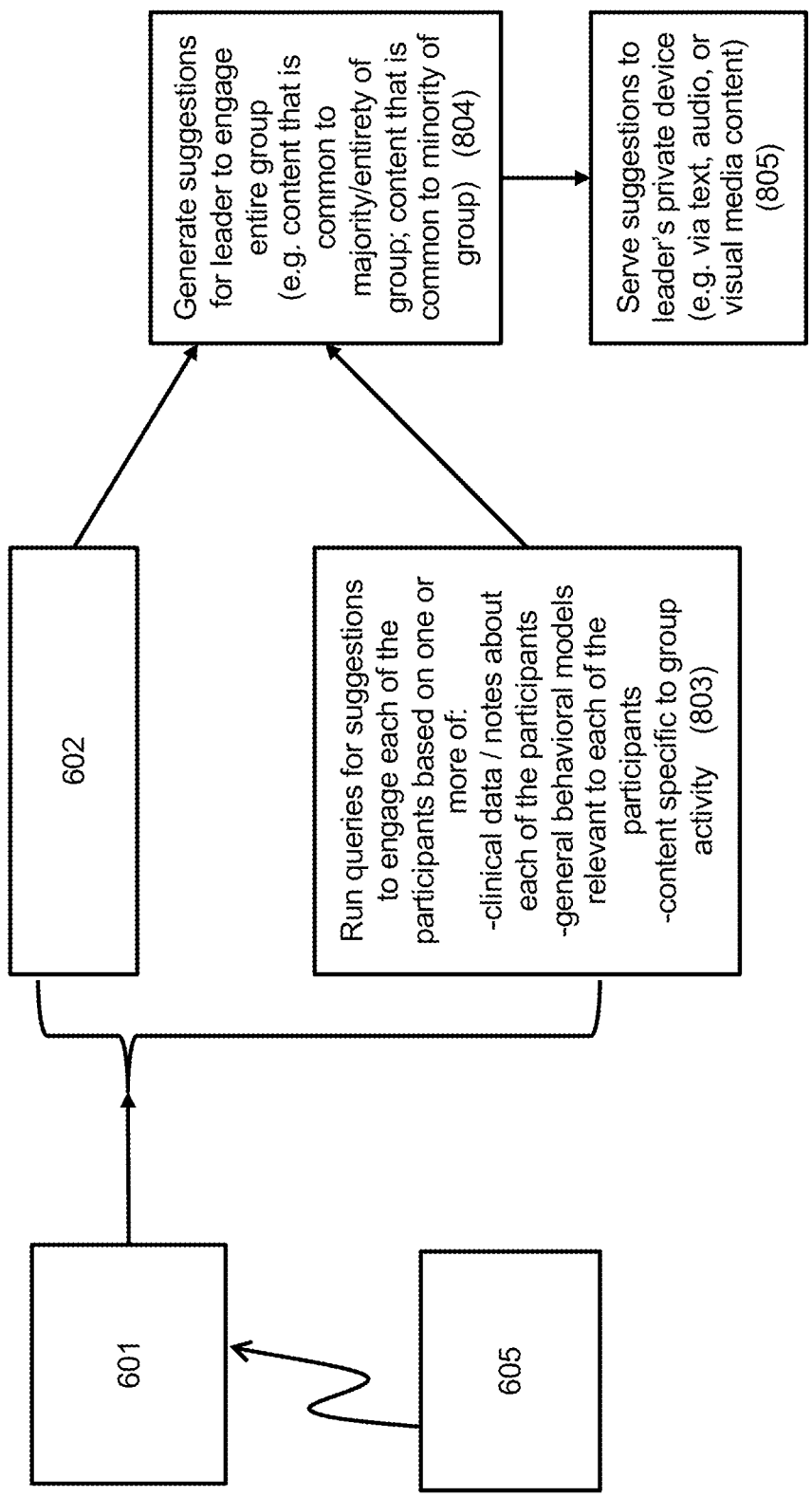
FIG. 8 is a flow diagram of example computer executable or processor implemented instructions for the computing system to generate and serve suggestions to a leader to engage the entire group of participants in a group session.

Turning to FIG. 8, another example embodiment is provided that is similar to FIG. 7. However, the executable instructions are for the data enablement platform providing suggestions and media content options that are applicable to the entirety of the group, or to the majority of the participants in the group.

In particular, in FIG. 8, the block 605, 601 and 602 are executed. At block 803, the data enablement platform runs queries for suggestions to engage each of the participants based on one or more of: clinical data/notes about each of the participants; general behavioral models relevant to each of the participants; content specific to group activity; emotional state or behavioral scores of each of the group participants.

At block 804, the data enablement platform generates one or more suggestions for the leader to engage the entire group. These suggestions can include, for example, a first media content that is common to majority/entirety of group, and a second media content that is common to the largest minority of the group. These suggestions, which include media content options, are served to the leader's private device for consideration by the leader (block 805).

It will be appreciated that the process for a leader to make oral notes can occur prior to a first group session, during the first group session, or after the first group session, or a combination thereof. These oral notes can be reviewed by the same leader, or by a different leader, prior to a second group session, during the second group session, or after the second group session, or a combination thereof. For example, the suggestion giving process in FIG. 7 or FIG. 8, or for both processes, could occur prior to a group session, during a group session or after a group session, or a combination thereof.

In an example embodiment, the suggestions are given to the leader of the group session in advance of the group session taking place. For example, a suggestion is for the leader to watch for Bob (a group participant) since he is agitated today as determined from other caregivers or from the data enablement platform's data analysis process of recorded data (e.g. audio data, visual data, text data, biological data, etc. recorded of Bob). In another example, a suggestion for the leader to give Alice (a group participant) more care since she is withdrawn, as noted from a previous group session. In another example, a suggestion for the leader to help Joe (another group participant) on his exercises to improve his flexibility. Another example suggestion is for the leader to keep the program shorter, as a lesson learned from the notes takes from the previous group session. It will be appreciated that other suggestions can be given in advance of the group session.

In another example embodiment, the group bot or the leader bot automatically summarizes in a report the occurrences, discussions, or moods, or a combination thereof, of the participants that were observed during the group session. The report also automatically includes suggestions generated by the data enablement platform. This automatically generated report includes, for example, the following:

Bob was agitated—automatically showed a private video and he calmed down

Alice was withdrawn—you (leader) spoke with her about her favorite trip to Europe and she talked more Joe—you (leader) spoke a lot with Joe about exercising—Recommend that Joe probably needs more help next time The leader can add to this group session summary report (e.g. add that Sue was happy; add that Lawrence with upset with Gregory; etc.).

Figure 9:
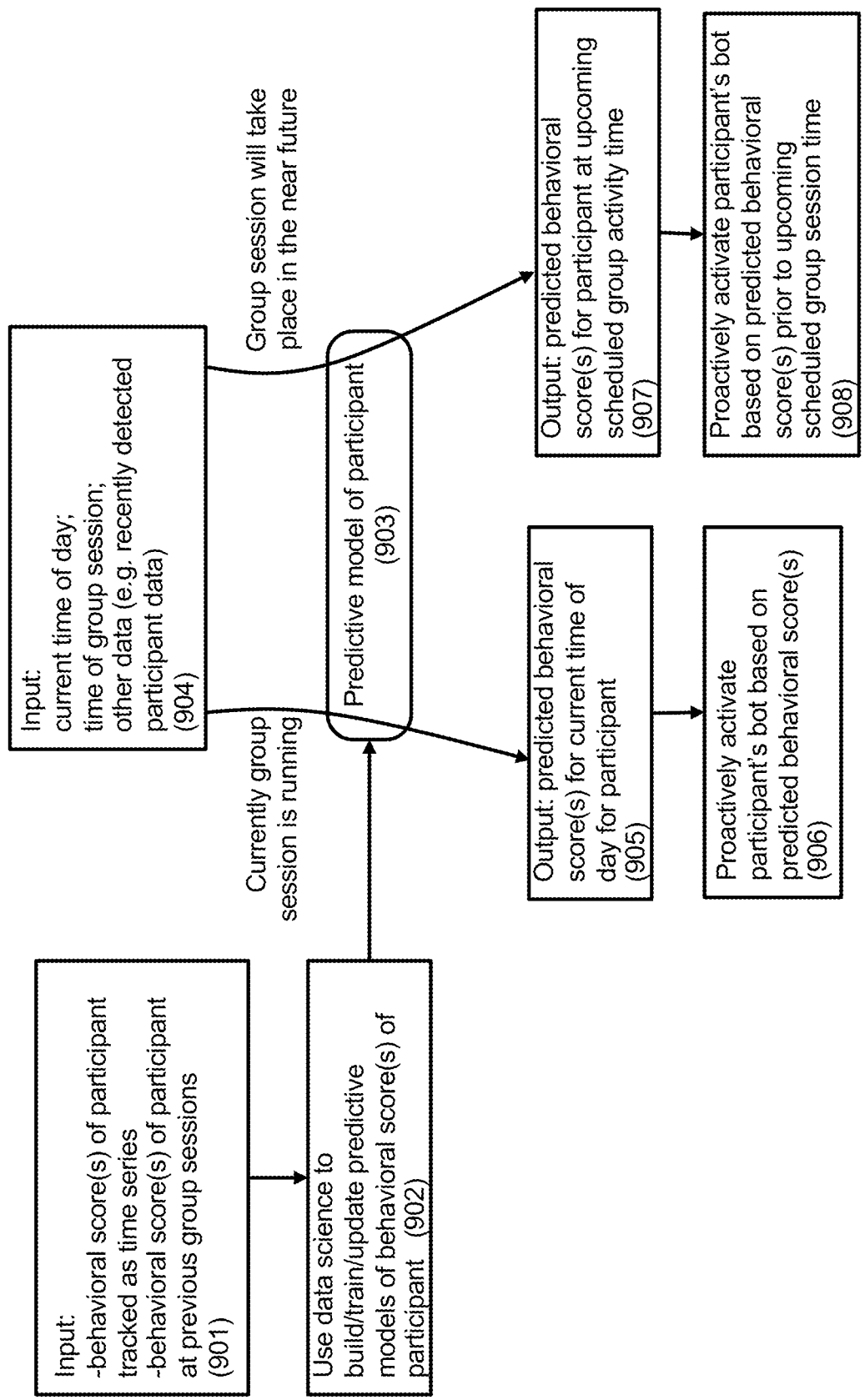
FIG. 9 is a flow diagram of example computer executable or processor implemented instructions for the computing system to predict one or more behavioral scores of a given participant, and to proactively serve media content to the given participant based on the current time of day or prior to a group session, or both.

Turning to FIG. 9, an example embodiment of executable instructions is provided for proactively engaging and preparing a participant for a group session via their own private device (e.g. P1's device 105) prior to the group session taking place. For example, if a participant P1 is predicted to be worried or aggressive during a scheduled group session, then the bot for P1 110 proactively engages the participant P1 before the group session starts to try to bring the participant P1 into a calmer and more relaxed emotional and cognitive state.

This embodiment is also used to proactively engage the participant during the group session based on predictive behavior modeling.

At block 901, the data enablement platform receives the input: behavioral score(s) of a participant tracked as a time series; or behavioral score(s) of the participant at previous group sessions; or both. At block 902, the data enablement platform uses data science to build, train, update, or a combination thereof, a predictive model of behavioral score(s) of the participant. This results in the predictive model of the participant 903.

After establishing the predictive model of the participant, at block 904, the data enablement platform obtains the input: the current time of day; the time of the group session (whether it is in the future or occurring now); and other data, such as recently detected data about the participant.

In one example embodiment, pursuant to block 904, it is determined that the group session is currently running. Using the predictive model of the participant 903, the data enablement platform outputs a predicted behavioral score or scores for the current time of day for the participant (block 905). The participant's bot is then proactively activated to engage the participant with their private media or public media, where the media is selected based on the predicted behavioral score or scores (block 906).

In another example embodiment, pursuant to block 904, it is determined that the group session will take place in the near future from the current time of day. Using the predictive model of the participant 903, the data enablement platform outputs what the behavioral score or scores will be at the future scheduled group session time for the participant (block 907). The participant's bot is then proactively activated to engage the participant with their private media or public media prior group session, where the media is selected based on what the behavioral score or scores will be at the time of the group session (block 908).

Figure 10:
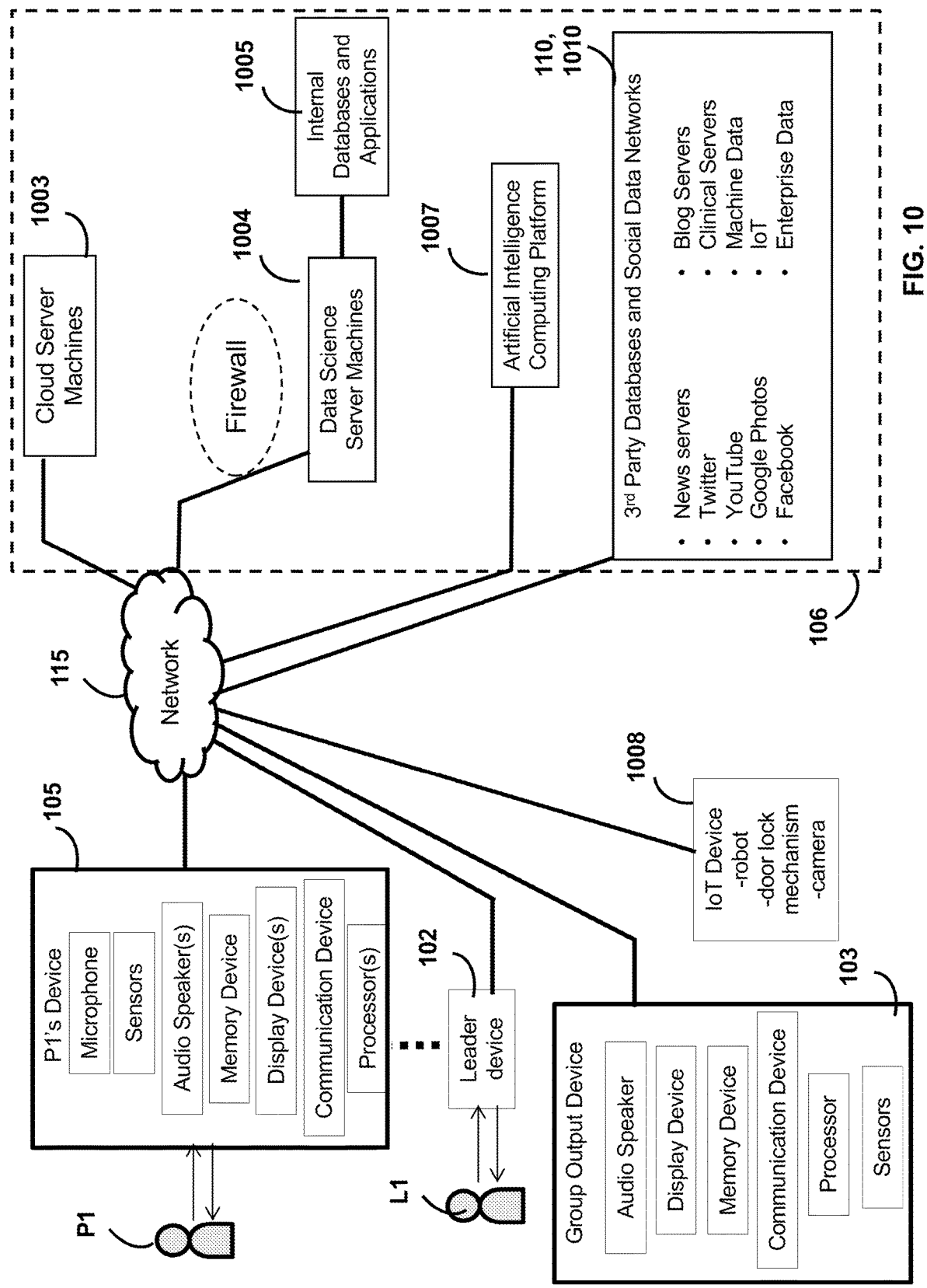
FIG. 10 is a schematic diagram of an example computing architecture.

Turning to FIG. 10, another example of the computing environment, including servers and the devices are shown in a more detailed configuration. The participant P1's user device 105, the leader's user device 102, the group output device 103, one or more IoT devices 1008, the cloud computing servers 1003, the data science servers 1004, AI computing platform 1007, and the various data sources 1010 are able to transmit and receive data via a network 115, such as the Internet. In an example embodiment, the data science servers 1004 and the internal applications and databases 1005 are in communication with each other over a private network for enhanced data security. In another example embodiment, the servers 1004 and the internal applications and the databases 1005 are in communication with each other over the same network 201.

As shown in FIG. 10, example components of the user device 105 include one or more microphones, one or more other sensors (e.g. cameras, infrared sensors, etc.), audio speakers, one or more memory devices, one or more display devices, a communication device, and one or more processors. The memory devices include, for example, RAM and ROM. The processors, for example, include one or more of: single core processors, multi-core processors, graphic processing units (GPUs), tensor processing units (TPUs), and neuromorphic chips. In an example embodiment, the one or more processors include a quantum processor, which can be used for various applications, including for executing data encryption and decryption computations to protect the user's data.

In an example embodiment, the user device's memory includes various "bots" that are part of the data enable application, which can also reside on the user device. For example, the bot for P1 110 also resides locally on P1's user device 105. These bots include processing that also resides on the 3rd party cloud computing servers 1003. Examples of chat bot technologies that can be modified or integrated (or both) into the system described herein include, but are not limited to, the trade names Siri, Google Assistant, Alexa, and Cortana.

The user device 102 for the leader includes similar components, or the same components, as the user device 105.

In this example embodiment, the cloud server machines 1003, the data science server machines 1004, the internal database and applications 1005, the artificial intelligence platform 1007, and the 3rd party databases and social data networks 1010 collectively form the data enablement platform 106.

Example general embodiments and related example aspects are provided below.

In an example embodiment, a computing system for assisting in group sessions is provided. The computing system includes: server system that comprises: a group bot comprising public group data and private group data; a first bot for a first participant in a group, comprising private data and public data associated with the first participant; and a leader bot for a leader of the group, the leader bot data interactive with the group bot and the first bot. The computing system also includes a mobile device, assigned to the leader, that accesses the leader bot on the server system. The mobile device receives user input to initiate a private mode or a public mode, wherein the public mode enables the leader bot to interact with the public group data and the public data associated with the first participant, and the private mode enables the leader bot to interact with the private group data and the private data associated with the first participant.

In an example aspect, via the mobile device, the leader bot commands the group bot to store notes about a given group session as part of the private group data.

In another example aspect, via the mobile device, the leader bot commands the first bot to serve media content from the private data associated with the first participant via a permissioned user device.

In another example aspect, the user input to initiate the private mode or the public mode is a voice input.

In another example aspect, the voice input is analysed for parameters comprising one or more of: volume of the voice input, tonality of the voice input, and sound frequency of the voice input.

In another example aspect, if the voice input is below a certain volume threshold, then the private mode is initiated.

In another example aspect, the mobile device comprises a camera, and the user input to initiate the private mode or the public mode comprises a facial expression detected by the camera.

In another example aspect, the mobile device comprises a camera, and the user input to initiate the private mode or the public mode comprises lip movements detected by the camera.

In another example aspect, the mobile device comprises a touch screen interface, and the user input to initiate the private mode or the public mode comprises a touch gesture detected by the touch screen interface.

In another example aspect, after the mobile device detects audio input that comprises a name of the first participant and a command, the leader bot interacts with the first bot.

In another example aspect, the command initiates the first bot to serve media content from the public data associated with the first participant via an output device that is in data communication with the server system; and wherein the output device is the mobile device or an ancillary device.

In another example aspect, the command initiates the first bot to serve media content; and, after the server system detects the command, the first bot obtains a behavioral score of the first participant, executes a query to select a specific media content associated with the first participant based on the behavioral score, and serves the specific media content on an output device that is in data communication with the server system; and wherein the output device is the mobile device or an ancillary device.

In another example aspect, the command initiates a session to record notes via the mobile device, and the notes are stored in the private data associated with the first participant.

In another example aspect, the notes are recorded orally using the mobile device.

In another example aspect, after the mobile device detects audio input that comprises a name of the first participant and a command, the server system determines whether the first participant is associated with their own private device; if the first participant is associated with their own private device, then the server system searches both the private data and the public data associated with the first participant to select and serve media content to play on the first participant's own private device.

In another example aspect, after the mobile device detects audio input that comprises a name of the first participant and a command, the server system determines whether the first participant is associated with their own private device; if the first participant is not associated with their own private device, then the server system searches both the public data associated with the first participant to select and serve media content to play on a group output device that is in data communication with the server system.

In another example aspect, the server system comprises a second bot for a second participant in the group, comprising private data and public data associated with the second participant; and the group bot combines the public data associated with the first participant with the public data associated with the second participant to generate new public group data.

In another example aspect, a group output device is in data communication with the server system, and the server system transmits the new public group data to the group output device.

In another example aspect, at a start or prior to the start of a group session, the mobile device automatically processes text notes about a previous group session using text-to-speech processing, and plays the text notes in audio format.

In another example aspect, at a start or prior to the start of a group session, the mobile device automatically displays notes about a previous group session in text format.

In another example embodiment, a computing system is provided for assisting interaction between a leader and a participant. The computing system includes a server system that comprises: a participant bot for the participant, comprising private data and public data associated with the participant; and a leader bot for the leader, the leader bot data interactive with the participant bot. The computing system also includes a mobile device, assigned to the leader, that comprises a microphone, an audio speaker, a display device, a communication device and a processor. The mobile device accesses the leader bot on the server system and the mobile device receives voice input to initiate a private mode or a public mode. The public mode enables the leader bot to interact with the public data associated with the participant, and the private mode enables the leader bot to interact with the private data associated with the participant.

In an example aspect, after the public mode is initiated, the mobile device detects an audio command that initiates the participant bot to serve media content from the public data associated with the participant via an output device that is in data communication with the server system; and wherein the output device is the mobile device or an ancillary device.

In another example aspect, after the private mode is initiated, the mobile device detects an audio command that initiates the participant bot to search in the private data and the public data associated for a specific media content, and then serve the specific media content via an output device that is in data communication with the server system; and wherein the output device is the mobile device or an ancillary device.

In another example aspect, responsive to the mobile device detecting an audio command to initiate the participant bot to serve media content; the participant bot obtains a behavioral score of the participant, executes a query to select a specific media content associated with the participant based on the behavioral score, and serves the specific media content on an output device that is in data communication with the server system; and wherein the output device is the mobile device or an ancillary device.

In another example aspect, the voice input is analysed for one or more parameters to determine whether to initiate the private mode or the public mode, the one or more parameters comprising one or more of: volume of the voice input, tonality of the voice input, and sound frequency of the voice input.

In another example aspect, if the voice input is below a certain volume threshold, then the private mode is initiated.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the servers or computing devices or accessible or connectable thereto. Any application or module herein described may be implemented using computer readable/executable instructions that may be stored or otherwise held by such computer readable media.

It will be appreciated that different features of the example embodiments of the system and methods, as described herein, may be combined with each other in different ways. In other words, different devices, modules, operations, functionality and components may be used together according to other example embodiments, although not specifically stated.

The steps or operations in the flow diagrams described herein are just for example. There may be many variations to these steps or operations according to the principles described herein. For instance, the steps may be performed in a differing order, or steps may be added, deleted, or modified.

It will also be appreciated that the examples and corresponding system diagrams used herein are for illustrative purposes only. Different configurations and terminology can be used without departing from the principles expressed herein. For instance, components and modules can be added, deleted, modified, or arranged with differing connections without departing from these principles.

Although the above has been described with reference to certain specific embodiments, various modifications thereof will be apparent to those skilled in the art without departing from the scope of the claims appended hereto.

The invention claimed is:

1. A computing system for assisting in group sessions, comprising:
    a server system that comprises: a group bot comprising public group data and private group data; a first bot for a first participant in a group, comprising private data and public data associated with the first participant; and a leader bot for a leader of the group, the leader bot interactive with the group bot and the first bot; and
    a mobile device, assigned to the leader, that is configured to access the leader bot on the server system, and the mobile device is configured to receive user input to initiate a private mode or a public mode, wherein the public mode enables the leader bot to interact with the public group data and the public data associated with the first participant, and the private mode enables the leader bot to interact with the private group data and the private data associated with the first participant.

2. The computing system of claim 1 wherein, via the mobile device, the leader bot commands the group bot to store notes about a given group session as part of the private group data.

3. The computing system of claim 1 wherein, via the mobile device, the leader bot commands the first bot to serve media content from the private data associated with the first participant via a permissioned user device.

4. The computing system of claim 1 wherein the user input to initiate the private mode or the public mode is a voice input.

5. The computing system of claim 4 wherein the voice input is analysed for parameters comprising one or more of: volume of the voice input, tonality of the voice input, and sound frequency of the voice input.

6. The computing system of claim 4 wherein if the voice input is below a certain volume threshold, then the private mode is initiated.

7. The computing system of claim 1 wherein the mobile device comprises a camera, and the user input to initiate the private mode or the public mode comprises a facial expression detected by the camera.

8. The computing system of claim 1 wherein the mobile device comprises a camera, and the user input to initiate the private mode or the public mode comprises lip movements detected by the camera.

9. The computing system of claim 1 wherein the mobile device comprises a touch screen interface, and the user input to initiate the private mode or the public mode comprises a touch gesture detected by the touch screen interface.

10. The computing system of claim 1 wherein, after the mobile device detects audio input that comprises a name of the first participant and a command, the leader bot interacts with the first bot.

11. The computing system of claim 10 wherein the command initiates the first bot to serve media content from the public data associated with the first participant via an output device that is in data communication with the server system; and wherein the output device is the mobile device or an ancillary device.

12. The computing system of claim 10 wherein the command initiates the first bot to serve media content; and, after the server system detects the command, the first bot obtains a behavioral score of the first participant, executes a query to select a specific media content associated with the first participant based on the behavioral score, and serves the specific media content on an output device that is in data communication with the server system; and wherein the output device is the mobile device or an ancillary device.

13. The computing system of claim 10 wherein the command initiates a session to record notes via the mobile device, and the notes are stored in the private data associated with the first participant.

14. The computing system of claim 13 wherein the notes are recorded orally using the mobile device.

15. The computing system of claim 1 wherein, after the mobile device detects audio input that comprises a name of the first participant and a command, the server system determines whether the first participant is associated with their own private device; if the first participant is associated with their own private device, then the server system searches both the private data and the public data associated with the first participant to select and serve media content to play on the first participant's own private device.

16. The computing system of claim 1 wherein, after the mobile device detects audio input that comprises a name of the first participant and a command, the server system determines whether the first participant is associated with their own private device; if the first participant is not associated with their own private device, then the server system searches both the public data associated with the first participant to select and serve media content to play on a group output device that is in data communication with the server system.

17. The computing system of claim 1 wherein the server system comprises a second bot for a second participant in a group, comprising private data and public data associated with the second participant; and the group bot combines the public data associated with the first participant with the public data associated with the second participant to generate new public group data.

18. The computing system of claim 17 wherein a group output device is in data communication with the server system, and the server system transmits the new public group data to the group output device.

19. The computing system of claim 1 wherein, at a start or prior to the start of a group session, the mobile device automatically processes text notes about a previous group session using text-to-speech processing, and plays the text notes in audio format.

20. The computing system of claim 1 wherein, at a start or prior to the start of a group session, the mobile device automatically displays notes about a previous group session in text format.

21. A computing system for assisting interaction between a leader and a participant, comprising:
   a server system that comprises: a participant bot for the participant, comprising private data and public data associated with the participant; and a leader bot for the leader, the leader bot data interactive with the participant bot; and
   a mobile device, assigned to the leader, that comprises a microphone, an audio speaker, a display device, a communication device and a processor; wherein the mobile device is configured to access the leader bot on the server system and the mobile device is configured to receive a voice input to initiate a private mode or a public mode; wherein the public mode enables the leader bot to interact with the public data associated with the participant, and the private mode enables the leader bot to interact with the private data associated with the participant.

22. The computing system of claim 21, after the public mode is initiated, the mobile device detects an audio command that initiates the participant bot to serve media content from the public data associated with the participant via an output device that is in data communication with the server system; and wherein the output device is the mobile device or an ancillary device.

23. The computing system of claim 21, after the private mode is initiated, the mobile device detects an audio command that initiates the participant bot to search in the private data and the public data associated for a specific media content, and then serve the specific media content via an output device that is in data communication with the server system; and wherein the output device is the mobile device or an ancillary device.

24. The computing system of claim 21, wherein, responsive to the mobile device detecting an audio command to initiate the participant bot to serve media content, the participant bot obtains a behavioral score of the participant, executes a query to select a specific media content associated with the participant based on the behavioral score, and serves the specific media content on an output device that is in data communication with the server system; and wherein the output device is the mobile device or an ancillary device.

25. The computing system of claim 21, wherein the voice input is analysed for one or more parameters to determine whether to initiate the private mode or the public mode, the one or more parameters comprising one or more of: volume of the voice input, tonality of the voice input, and sound frequency of the voice input.

26. The computing system of claim 21, wherein if the voice input is below a certain volume threshold, then the private mode is initiated.

* * * * *